United States Patent [19]

Koltringer

[11] Patent Number: 5,532,269
[45] Date of Patent: Jul. 2, 1996

[54] PREPARATION FOR TREATING CIRCULATORY CHANGES

[75] Inventor: Peter Koltringer, Graz, Austria

[73] Assignee: ASTA Medica Aktiengesellschaft, Dresden, Germany

[21] Appl. No.: 320,400

[22] Filed: Oct. 11, 1994

[30] Foreign Application Priority Data

Oct. 11, 1993 [AT] Austria ..................................... 2045/93
Oct. 18, 1993 [AT] Austria ..................................... 2094/93

[51] Int. Cl.$^6$ ................................................. A01N 43/26
[52] U.S. Cl. ............................................................ 514/440
[58] Field of Search ............................................. 514/440

[56] References Cited

PUBLICATIONS

CA 116:168213 1992.
CA 112:240492 1989.
CA 79:62158 1973.
CA:72:98714.
Biological Abstracts (BA) 82:270869 (1982.

Primary Examiner—Paul J. Killos
Attorney, Agent, or Firm—Cushman, Darby & Cushman

[57] ABSTRACT

The invention is relative to a preparation in a novel indication which reduces the formation of deposits of thrombocytes in the vascular system. This prevents the occurrence of constrictions in the vessels. The preparation is alpha-lipoic acid (thioctic acid), which can be administered in several forms of administration such as, e.g., by injection or by tablet and which is largely free of side effects.

Moreover, it can be shown in the case of smokers that the substance has a prophylactic effect in that the typical supersensitivity of the thrombocytes, which constitutes a cause for the appearance of premature vessel changes, is braked.

13 Claims, No Drawings

PREPARATION FOR TREATING CIRCULATORY CHANGES

α-lipoic acid (=thioctic acid) is chemically 1,2-dithiacyclopentane-3-valeric acid. The production of the free R-thioctic acid is described, e.g., in DE-OS 41 37 773.

The invention is relative to R,S-thioctic acid in reduced or oxidized form, its isolated enantiomers (R-thioctic acid and S-thioctic acid) and metabolites in the form of the free acid as salts, esters or amides. Thioctic acid is a component of the cell metabolism and is therefore found in many plants and animal organisms. It acts as one of the coenzymes in the oxidative decarboxylation of pyruvate and other α-keto acids. Thioctic acid has been used for some time in various diseases, among others, diseases of the liver, liver damage due to mushroom poisoning and in diabetic and alcoholic polyneuropathy, a change of peripheral nerves accompanying metabolic diseases.

The chemistry and biochemistry of α-lipoic acid are discussed in the article by Schmidt, Grafen and Goedde, Ang. Chem. 77 (1965), pp. 900–911 and in Reed, Vitamins, Hormones 20 (1962), pp. 1–38.

The biosynthesis of derivatives of α-lipoic acid is discussed by Gunsalus, Barton and Gruber in J. Amer. Chem. Soc. 78 (1956) pp. 1763–1766.

The present invention is relative to a substance which offers good effects in a novel application for the treatment of circulatory changes, for example, changes in the blood flow and circulation, resulting in deposits on vessel walls.

Such circulatory changes are present in many diseases, a few of which are cited in the following by way of example:
 a) Smokers
 b) Diabetics
 c) Lipometabolic disturbances.

The preparation for preventing the progression of circulatory contains alpha-lipoic acid (R,S-thioctic acid) in a minimum intravenous dosage amount of 50 mg or minimum oral dosage amount of 20 mg.

Furthermore, the preparation in accordance with the invention is suitable for prophylactic use in the above-mentioned patients in order to prevent these changes from occurring at all, which can lead clinically to the development of high blood pressure.

PHARMACOLOGICAL EXAMPLE 1

Male Wistar rats with an average initial weight of approximately 120 g were used. The control animals received standardized rat food, 30 animals (10 per group) received 10 g/animal/day of a special cardiovasopathogenic diet (see below for composition). Water was available for the animals ad libitum. One group (10 animals) was treated daily with 0.5 ml/100 g 0.9% NaCl solution i.p. The animals of the two other groups (10 rats each) were treated daily with thioctic acid (15 and 30 mg/kg) i.p. The blood pressure was measured indirectly (non-invasively) at weekly intervals with the aid of a suitable blood pressure instrument (sphygmomanometer).

| Group | Rise in blood pressure after 7 weeks (mm Hg) |
| --- | --- |
| Control | 3.5 |
| Pathogenic diet | 31.4 |
| 15 mg/kg | 14 |
| 30 mg/kg | 14.5 |

The test was carried out in accordance with the method of I. Szelenyi, J., Sos and J. Rigo "Action of Magnesium Orotate and Orotic Acid on the Elevation of Blood Pressure Initiated in Animal Experiments and Cardiopathogenic Changes in the Heart Muscle" (Deutsches Medizinisches Journal, 21st year, vol. 22—Berlin, Nov. 20, 1970).

Many of the diseases cited above begin slowly and without clear symptoms. Problems with the legs frequently occur independently of the basic disease. The patients must often remain standing because they have severe pains. However, there are also changes in the heart which can result in angina pectoris up to infarct and changes in the brain which can cause temporary inadequate circulation in mild cases or can be expressed in the form of paralyses or other neurological symptoms in time.

The active mechanism of the appearance of vessel changes which adversely affect the circulation as a consequence takes place to an essential degree via the blood platelets, which are designated in medicine as thrombocytes. The blood platelets have a physiological function of repairing tissue damage in which they accumulate where collagen is present. This means for the vascular system that collagen is offered at locations where the inner layer is defective and healthy thrombocytes accumulate in order to make possible jacketing and regeneration. In the case of certain diseases and especially in the case of smokers the individual thrombocyte is supersensitive, that is, it reacts readily with extremely small amounts of collagen with accumulation on the vessel wall. This has the consequence that thrombocytes are superimposed on a practically healthy vessel wall, thus constricting the vessel. This results subsequently in an obligatory decrease in the flow.

The present invention is directed to a remedy in this connection. In this regard, the invention provides alpha-lipoic acid (thioctic acid) as a substance which selectively inhibits the supersensitive thrombocytes as to thrombocyte function and normalizes their physiological functions. In comparison to other substances which also act on the thrombocyte function, hardly any side effects occur with alpha-lipoic acid.

Alpha-lipoic acid, also called thioctic acid, is commercially admitted in the form of tablets and of ampoules; the dosage in the case of tablets is approximately 200 mg and in the case of ampoules the dosage fluctuates on the order of 10 mg to 50 mg/ml. The main areas of indication are diabetic polyneuropathy as well as, in some countries, certain diseases of the liver.

It turned out in the case of smokers that alpha-lipoic acid, when prophylactically administered, eliminates to a large extent the effect of increasing the thrombocyte function typical for smokers. In addition, a distinctly better circulation of the skin was also found in numerous smokers with alpha-lipoic acid.

In the case of patients with dysglycemia (diabetes mellitus) it turned out that in the early stage largely normal thrombocyte functions likewise occur for a rather long time, which appears to be unusual and speaks for an improved circulation.

Based on previous clinical experiences, there are indications that the subject of the invention inhibits the increase of circulatory disturbances and the development of high blood pressure and on the other hand, when administered prophylactically to diabetics, the appearance of these disturbances is significantly delayed.

The invention is explained in detail in the following in examples.

EXAMPLE 2

It turned out in the case of smokers with intravenous administration of 1 ampoule alpha-lipoic acid over 7 days that the levels of thrombocyte function on collagen were inconspicuous but in a group of smokers of the same age without alpha-lipoic acid distinctly higher values were registered. Additional measurements of circulation carried out on the skin of the legs showed distinctly higher values in the alpha-lipoic acid group than without alpha-lipoic acid, which indicates an improvement of circulation in the microcirculation.

EXAMPLE 3

The values of the thrombocyte function were determined in a volunteer test subject (non-smoker), which were inconspicuous. After the smoking of 1 cigarette, distinctly higher values were found. The same experiment was repeated on the next day in which a dose of 400 mg alpha-lipoic acid had been taken previously in tablet form. There was no increase in the values.

EXAMPLE 4

Alpha-lipoic acid was administered for 1 week to patients who had diabetes for several years. This group exhibited inconspicuous thrombocyte levels. On the other hand, a largely identical control group exhibited distinctly higher values.

What I claim is:

1. A preparation for the treatment of circulatory changes which comprises essentially alpha-lipoic acid (R,S-thioctic acid) in reduced or oxidized form, its isolated enantiomers and metabolites in the form of the free acid, as salts, esters or amides wherein the alpha-lipoic acid is present in a dosage amount of 20 mg–1800 mg.

2. The preparation for preventing the progression of circulatory changes according to claim 1 wherein the alpha-lipoic acid (R,S-thioctic acid) is present in a minimum intravenous dosage amount of 50 mg.

3. The preparation for preventing the progression of circulatory changes according to claim 1, wherein the alpha-lipoic acid (R,S-thioctic acid) is present in a minimum oral dosage amount of 20 mg.

4. A method for the alleviation of circulatory changes comprising administering to a patient a composition according to claim 1 over a period of at least 7 days to achieve the circulatory change.

5. A method for the alleviation of circulatory changes according to claim 4 wherein the mammal is a smoker, diabetic or patient with lipometabolic disturbance.

6. A method for inhibiting the accumulation of thrombocytes on blood vessel walls comprising administering the preparation according to claim 1 to a mammal in an inhibitory amount.

7. A method for the alleviation of circulatory changes comprising administering to a patient a composition according to claim 1 wherein the patient is a smoker.

8. A method for the alleviation of circulatory changes according to claim 7 wherein the dosage amount is between 50 mg and 1800 mg.

9. A method for the alleviation of circulatory changes according to claim 7 wherein the dosage amount is between 50 mg and 400 mg.

10. The preparation of claim 1 wherein the alpha-lipoic acid is present in a dosage amount of 50 mg–1800 mg.

11. The preparation of claim 1 wherein the alpha-lipoic acid is present in a dosage amount of 15 mg/kg patient– 30 mg/kg patient.

12. The preparation of claim 1 wherein the alpha-lipoic acid is present in a dosage amount of 20 mg–400 mg.

13. A method for the alleviation of circulatory changes comprising administering to a patient a composition according to claim 1 wherein the patient has diabetes of Type I or Type II or insulin resistance.

* * * * *